United States Patent
Takama et al.

(10) Patent No.: US 9,357,913 B2
(45) Date of Patent: Jun. 7, 2016

(54) OPHTHALMOLOGIC IMAGE DISPLAY APPARATUS, OPHTHALMOLOGIC IMAGE DISPLAY METHOD, PROGRAM, AND STORAGE MEDIUM

(71) Applicant: CANON KABUSHIKI KAISHA, Tokyo (JP)

(72) Inventors: Yasufumi Takama, Kawasaki (JP); Yoshihiko Iwase, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/264,813

(22) Filed: Apr. 29, 2014

(65) Prior Publication Data

US 2014/0233823 A1    Aug. 21, 2014

Related U.S. Application Data

(63) Continuation of application No. 13/028,012, filed on Feb. 15, 2011, now Pat. No. 8,744,158.

(30) Foreign Application Priority Data

Feb. 17, 2010 (JP) ................................. 2010-032696
Nov. 26, 2010 (JP) ................................. 2010-264221

(51) Int. Cl.
    *G06K 9/00* (2006.01)
    *A61B 3/00* (2006.01)
    *G06T 7/00* (2006.01)
    *G06F 19/00* (2011.01)

(52) U.S. Cl.
    CPC ............. *A61B 3/0025* (2013.01); *G06T 7/0012* (2013.01); *G06T 7/0016* (2013.01); *G06F 19/321* (2013.01); *G06T 2200/04* (2013.01); *G06T 2207/10101* (2013.01); *G06T 2207/30041* (2013.01)

(58) Field of Classification Search
    None
    See application file for complete search history.

(56) References Cited

U.S. PATENT DOCUMENTS

2007/0103693 A1*  5/2007  Everett et al. ................. 356/479
2010/0128960 A1*  5/2010  Yumikake .................... 382/133

FOREIGN PATENT DOCUMENTS

| JP | 2007252692 A | 10/2007 | |
| JP | PCT/JP2008/001511 | * 1/2009 | ............... A61B 3/12 |
| WO | 2009034705 A1 | 3/2009 | |

* cited by examiner

*Primary Examiner* — Atiba O Fitzpatrick
(74) *Attorney, Agent, or Firm* — Canon U.S.A. Inc., IP Division

(57) ABSTRACT

An ophthalmologic image display apparatus for displaying information about an eye includes an input unit configured to input a tomographic image of the eye, an acquisition unit configured to acquire diagnostic supporting information associated with positional information about the tomographic image of the eye, a processing unit configured to perform processing for assigning a voxel value to volume data constituting the tomographic image based on a reflection intensity value indicating the tomographic image and the diagnostic supporting information, and a display control unit configured to cause a display unit to display an image processed by the processing unit.

15 Claims, 7 Drawing Sheets

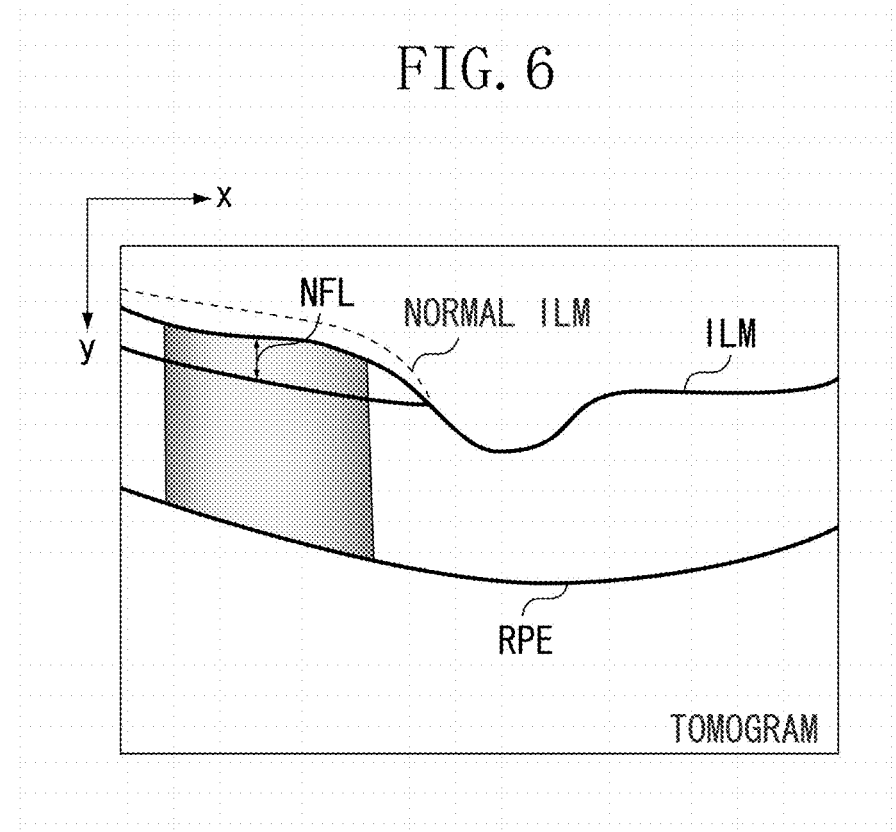

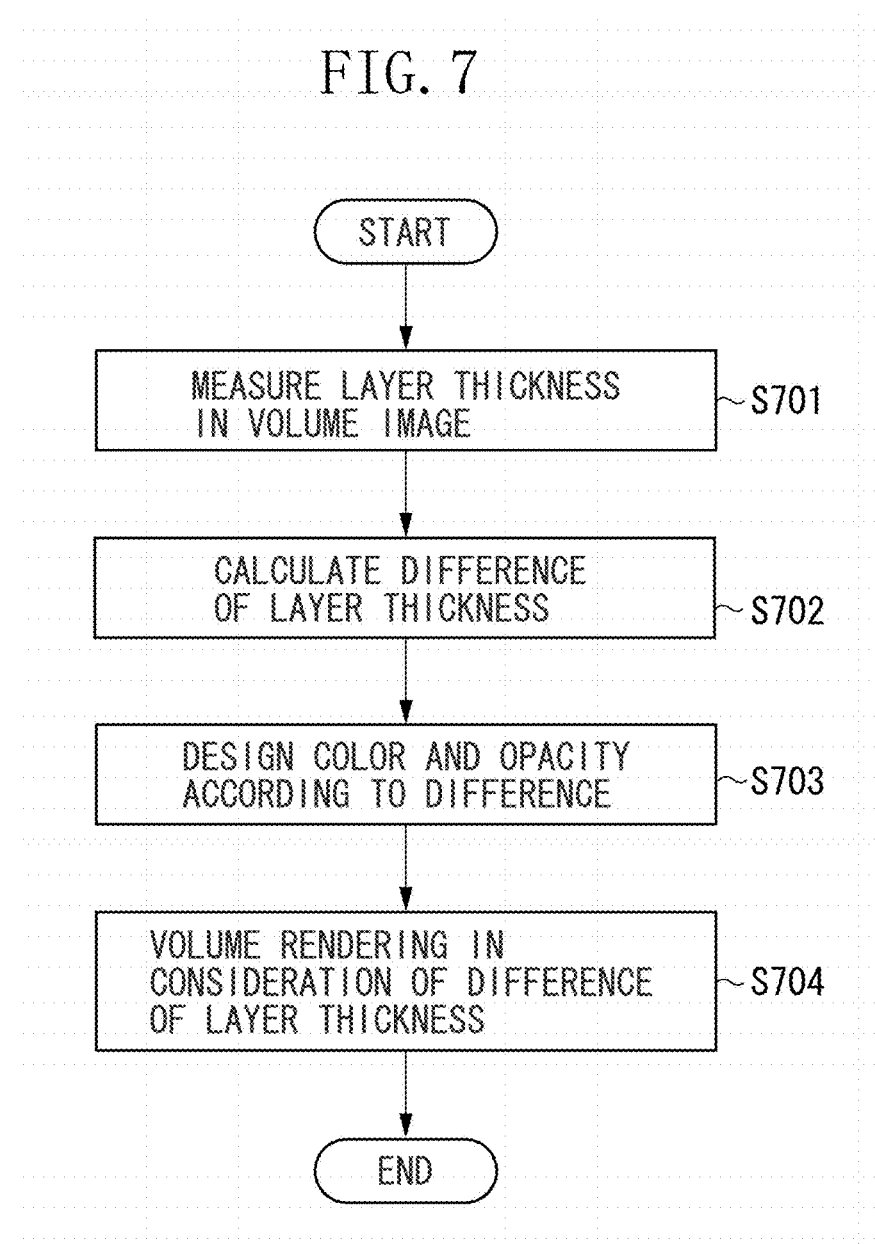

OPHTHALMOLOGIC IMAGE DISPLAY APPARATUS, OPHTHALMOLOGIC IMAGE DISPLAY METHOD, PROGRAM, AND STORAGE MEDIUM

CROSS REFERENCE TO RELATED APPLICATIONS

This application is a Continuation of U.S. patent application Ser. No. 13/028,012 filed Feb. 15, 2011, which claims priority to Japanese Patent Application No. 2010-264221 filed Nov. 26, 2010, and Japanese Patent Application No. 2010-032696 filed Feb. 17, 2010, each of which are hereby incorporated by reference herein in their entireties.

BACKGROUND OF THE INVENTION

1. Field of the Invention

The present invention relates to a technique for displaying an ophthalmologic image for use in, for example, an ophthalmologic medical care.

2. Description of the Related Art

An imaging apparatus referred to as an optical coherence tomography (hereinafter referred to as "OCT") has enabled acquisition of a three-dimensional retina image formed by volume rendering based on a plurality of two-dimensional tomographic images obtained by scanning an entire retina. It is known that a large number of fundus diseases such as glaucoma cause abnormality in the structure of a retina, and therefore the OCT is expected to be effective for a diagnosis of a disease and a follow-up observation in the ophthalmologic medical field. Further, in recent years, the OCT has been used in imaging not only a fundus diagnosis but also an anterior eye portion such as a cornea.

In a tomographic image, a value of a reflection intensity of light from, for example, a retina is observed as an image. Therefore, a tomographic image is suitable for an observation of a tissue, but may be difficult to be used to grasp, for example, a change in a tissue over time, an overall spread of a disease, and a portion to be focused on, without an additional help.

Japanese Patent Application Laid-Open No. 2009-66015 discusses a technique which displays a tomographic image and layer thickness distribution information arranged side by side. Using the technique, the layer thickness distribution information and the tomographic image can be compared. Japanese Patent Application Laid-Open No. 2009-66015 further discusses a method for indicating a vascular territory. If a vessel exists in a retina, the light of the OCT cannot reach a deep portion, resulting in generation of a low-quality tomographic image. Therefore, Japanese Patent Application Laid-Open No. 2009-66015 indicates a need for a user to observe a retina while taking this matter into consideration.

However, the method discussed in Japanese Patent Application Laid-Open No. 2009-66015 can be used for comparison between a tomographic image and a layer thickness, and it is difficult to grasp, for example, how much a lesion has progressed from the tomographic image by this method.

SUMMARY OF THE INVENTION

The present invention is directed to a system for supporting a doctor's diagnosis by adding easily understandable diagnostic supporting information to a retina image formed by volume rendering. Further, the present invention is directed to providing diagnostic supporting information based on layer thicknesses of corresponding portions in a current retina image and a previously captured retina image.

According to an aspect of the present invention, an ophthalmologic image display apparatus for displaying information about an eye includes an input unit configured to input a tomographic image of the eye, an acquisition unit configured to acquire diagnostic supporting information associated with positional information about the tomographic image of the eye, a processing unit configured to perform processing for assigning a voxel value to volume data constituting the tomographic image based on a reflection intensity value indicating the tomographic image and the diagnostic supporting information, and a display control unit configured to cause a display unit to display an image processed by the processing unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 6 schematically illustrates a retina image with a difference from a standard layer thickness superimposed thereon.

FIG. 7 is a flowchart illustrating a processing procedure of the ophthalmologic image display apparatus.

DESCRIPTION OF THE EMBODIMENTS

Various exemplary embodiments, features, and aspects of the invention will be described in detail below with reference to the drawings.

The description which will be provided below is about exemplary embodiments of an ophthalmologic image display apparatus according to the present invention, and it should be noted that these embodiments are not intended to limit the present invention.

Figure 1:
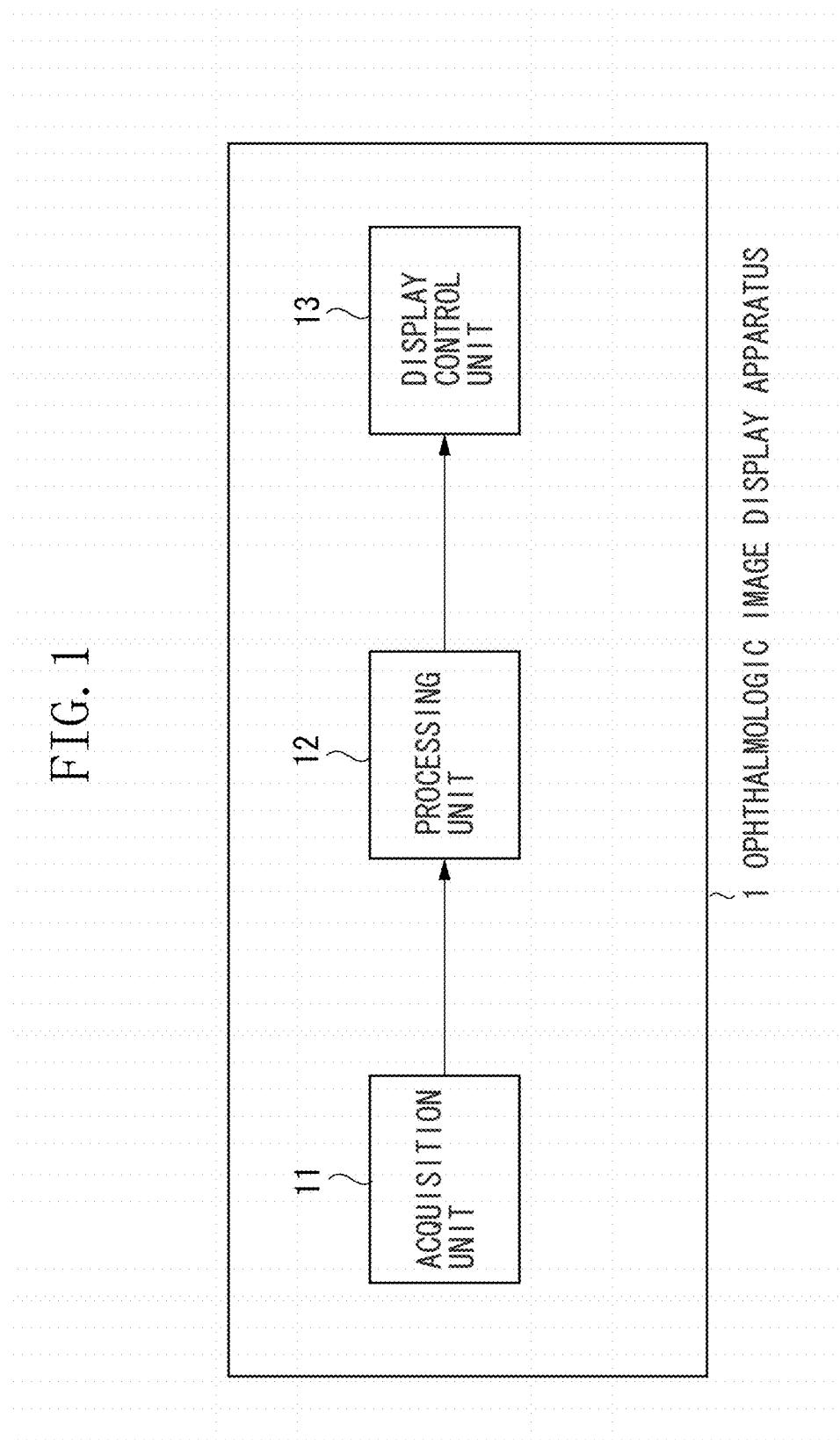
FIG. 1 illustrates a functional configuration of an ophthalmologic image display apparatus.

FIG. 1 illustrates a configuration of an ophthalmologic image display apparatus 1 according to a first exemplary embodiment. The ophthalmologic image display apparatus 1 includes an acquisition unit 11, a processing unit 12, and a display control unit 13.

In the present exemplary embodiment, the acquisition unit 11 measures layer thicknesses of a retina from tomographic images of the retina captured at different points in time, or acquires the measured results. A plurality of two-dimensional tomographic images of a retina can be acquired by scanning the retina a plurality of times. The tomographic image of the retina is constituted based on a value indicating intensity of light reflected by the eye. A three-dimensional retina tomographic image is formed from the plurality of two-dimensional retina tomographic images. Then, the value indicating the light intensity of the two-dimensional retina tomographic image is assigned to each voxel as a voxel value to obtain volume data.

Then, a difference between the layer thicknesses in the corresponding tomographic images captured at different points in time is acquired as a difference value. The processing unit 12 adds diagnostic supporting information to the volume data based on the difference value as the diagnostic supporting information. The display control unit 13 controls a monitor, which is a not-shown display unit, to display the image processed by the processing unit 12.

The ophthalmologic image display apparatus 1 can support a diagnosis of a doctor by, for example, enabling the doctor to easily locate a portion to be compared by the above-described way. More specifically, a boundary of a nerve fiber layer (hereinafter referred to as "NFL") is extracted from each of the tomographic images or volume data of a same subject captured at different time points to measure a thickness of the NFL therein. Next, a difference between the extracted NFL thicknesses is calculated. A color corresponding to the difference value is applied to a pixel in the volume data or the tomographic image based on the calculated value of the difference in layer thickness, and the colored data is displayed. Accordingly, it is possible to easily locate and compare a portion where the layer thickness is changed over time due to a disease. In the following, one usage of the present exemplary embodiment will be described in which a layer thickness of an NFL is used as a comparison target. However, information added to volume data or a tomographic image is not limited to the layer thickness of an NFL. The ophthalmologic image display apparatus 1 may measure a thickness of another layer constituting a retina or a cornea, or a thickness of a retina or a cornea as a whole, and use it as a comparison target.

Figure 2:
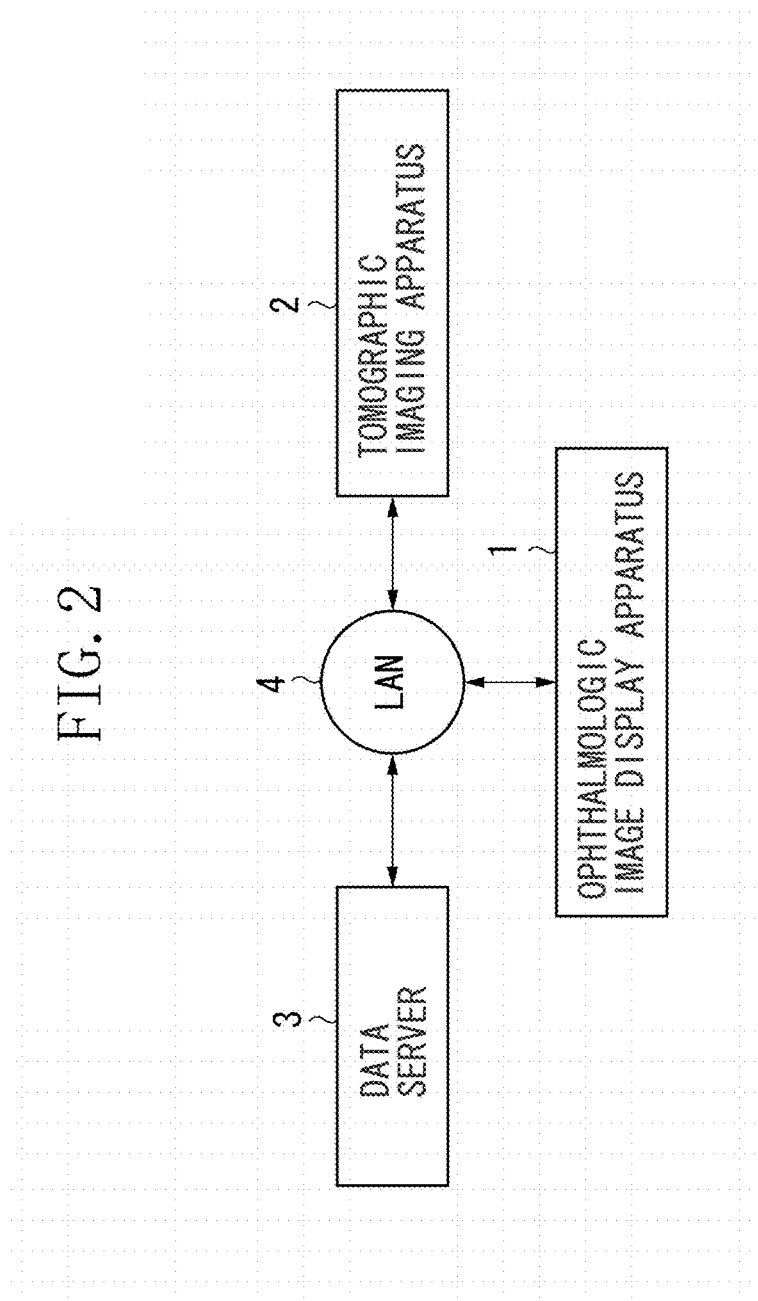
FIG. 2 illustrates a configuration of apparatuses connected to the ophthalmologic image display apparatus.

FIG. 2 illustrates a configuration of apparatuses connected to the ophthalmologic image display apparatus 1 according to the present exemplary embodiment. As illustrated in FIG. 2, the ophthalmologic image display apparatus 1 is connected to a tomographic image capturing apparatus 2 and a data server 3 via a local area network (LAN) 4 such as the Ethernet (registered trademark). The tomographic image capturing apparatus 2 is an apparatus for capturing a tomographic image of an eye, and is embodied by, for example, an OCT. Since an OCT acquires a tomographic image of each scanning line by one imaging operation, it is possible to acquire tomographic images corresponding to a plurality of scanning lines. Volume data of a retina can be acquired by arranging these tomographic images in the captured order.

The tomographic image capturing apparatus 2 captures a tomographic image of a subject (patient) according to an operation of a user (technician or doctor), and outputs acquired volume data to the ophthalmologic image display apparatus 1. Further, the ophthalmologic image display apparatus 1 may be configured to be connected to the data server 3 storing the volume data acquired by the tomographic image capturing apparatus 2 to obtain required volume data from the data server 3. The ophthalmologic image display apparatus 1 may be connected to those apparatuses via an interface such as a universal serial bus (USB) or Institute of Electrical and Electronics Engineers (IEEE) 1394. Further, the ophthalmologic image display apparatus 1 may be connected to those apparatuses via an external network such as the Internet with use of the LAN 4.

Figure 5:
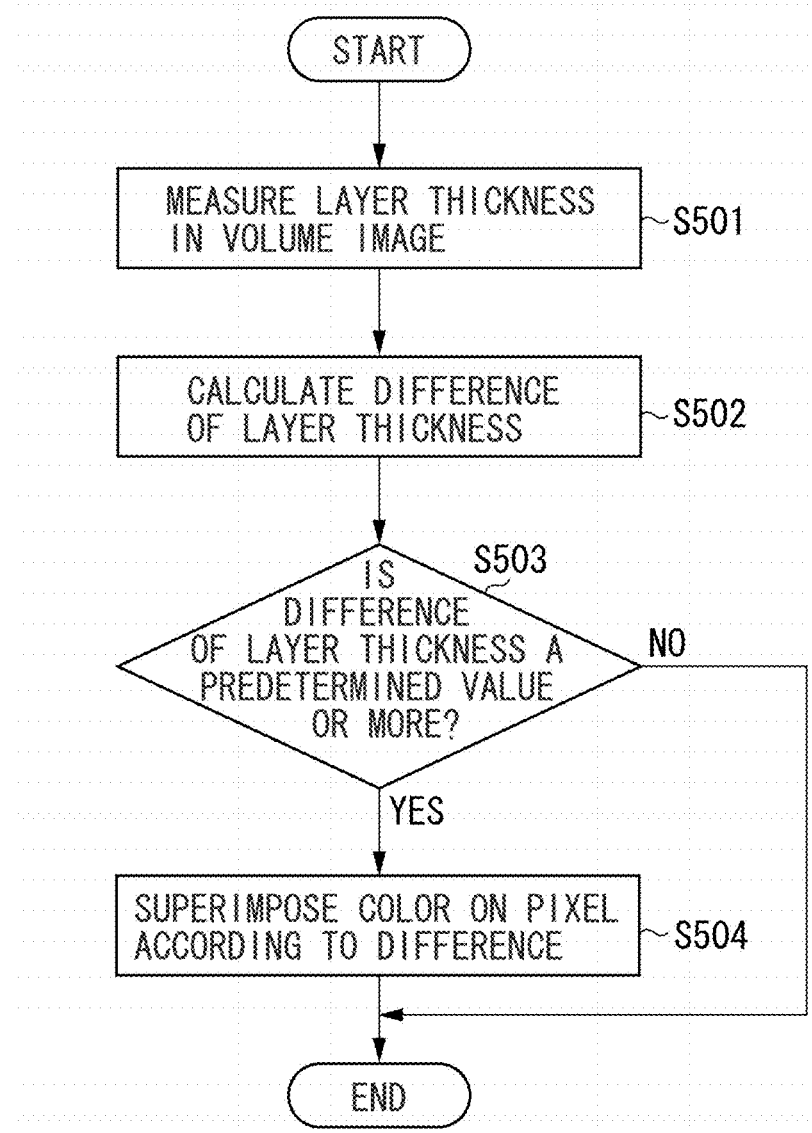
FIG. 5 is a flowchart illustrating a processing procedure of the ophthalmologic image display apparatus.

Next, a processing procedure of the ophthalmologic image display apparatus 1 according to the present exemplary embodiment will be described with reference to the flowchart illustrated in FIG. 5.

In step S501, first, the acquisition unit 11 acquires a plurality of pieces of volume data acquired by the tomographic image capturing apparatus 2 or volume data stored in the data server 3 that were captured at different time points. For convenience of description, it is assumed that, as the coordinate system of volume data, a horizontal direction of a tomographic image is an X axis and a vertical direction of a tomographic image is a Y axis.

Figure 3:
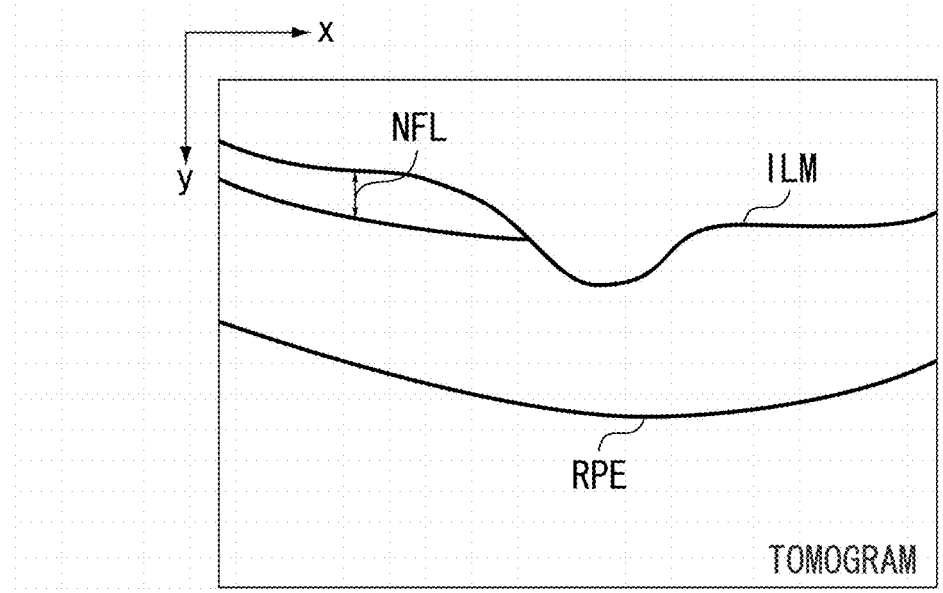
FIG. 3 schematically illustrates a layer structure in a tomographic image of a retina.

Next, an inner limiting membrane (hereinafter referred to as "ILM"), a lower end of an NFL layer, and a retinal pigment epithelium (hereinafter referred to as "RPE") are extracted from each volume data, as illustrated in the retina schematic diagram in FIG. 3. For acquiring boundaries among these layers, edge components are detected from the retina volume data, and several lines are extracted as candidates of the layer boundaries based on connectivity of the edge components. An uppermost line is selected as an ILM boundary, and the next line is selected as an NFL boundary from those candidates.

A method for extracting the layer boundaries is not limited to the above-described method, and may be realized by any method capable of extracting the boundaries among the layers from retina volume data. Finally, a thickness between the ILM and the lower end of the NFL is acquired from the extraction results as the layer thickness of the NFL.

In step S502, the acquisition unit 11 calculates the difference in the layer thickness in the X coordinate by subtracting the layer thickness of the NFL layer in the X coordinate in one piece of volume data from the thickness of the NFL in the X coordinate in another piece of volume data. Here, it is assumed that these two pieces of volume data is data capturing a same position, or their positions are adjusted and their coordinate systems correspond to each other. The position adjustment of the volume data pieces can be performed by a known method, for example, a method with use of a correlation coefficient. The processing in step S502 enables acquisition of the difference in the layer thickness, i.e., the difference between the thicknesses of the layers as the diagnostic supporting information associated with positional information of the volume data or the tomographic image of the eye.

In step S503, volume rendering is realized by applying opacity to the voxel value of each voxel.

Figure 4A:
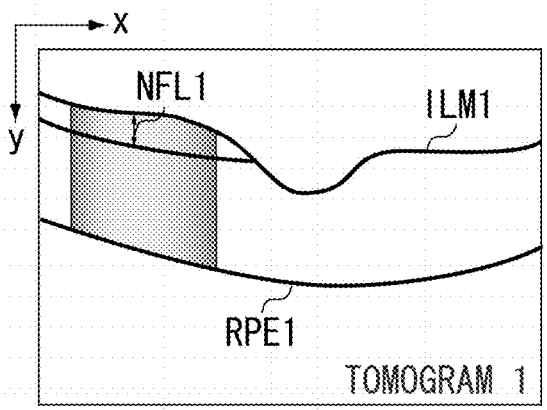
FIGS. 4A and 4B schematically illustrate a retina image with a difference in layer thickness superimposed thereon.
Figure 4B:
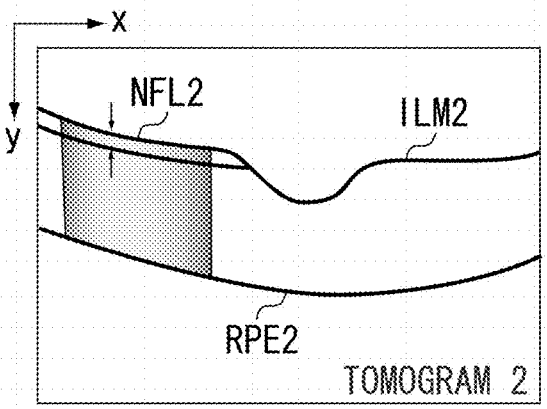

In step S504, color and opacity according to the difference are applied to the pixels in each volume data or pixels from the ILM to RPE in the tomographic image as illustrated in FIG. 4, and the applied color and opacity are displayed. In glaucoma or another disease that causes reduction in the layer thickness as the disease progresses, for example, the color and the opacity may be set so that a portion with a large difference in the layer thickness becomes redder, and has a larger opacity than a value determined based on the voxel value. As a result, the tomographic image is displayed in such a manner that a portion with a significantly reduced layer thickness becomes redder and more opaque. On the other hand, a portion with a slightly or seldom reduced thickness is displayed as the tomographic image formed using the voxel value of the volume data without any change. Further, for a portion with an increased thickness as time has passed, the color and the opacity can be set so that the portion with a larger difference in layer thickness becomes bluer, and has a larger opacity.

As a result, the tomographic image is displayed in such a manner that a portion with a significantly increased layer thickness becomes bluer and more opaque. On the other hand, a portion with a slightly or seldom increased thickness is displayed as the tomographic image formed using the voxel value of the volume data without any change. A portion in which a change in the layer thickness is smaller than a predetermined value is displayed using the voxel value as it is. When the processing in steps S503 and S504 are executed for all voxels of the volume data, the color can be superimposed and displayed onto the portion with a significant change in the layer thickness in the tomographic image.

Since it is extremely important to find an object to be closely observed from volume data, addition of information onto a tomographic image is effective.

Then, the display control unit 13 performs display control so that the monitor as the not-illustrated display unit displays the image processed by the processing unit 12.

According to the present exemplary embodiment configured as described above, it is possible to easily recognize and compare, on the tomographic image, a position and a change amount of the layer thickness of a portion where a disease has progressed or a portion where a treatment has succeeded.

The present exemplary embodiment is described based on an example of measuring the layer thicknesses in two pieces of the volume data in step S501, and indicating the difference between the layer thicknesses on the tomographic image. However, the present invention is not limited to this example. For example, the ophthalmologic image display apparatus 1 may measure the thicknesses of the layers in three pieces of volume data A, B, and C, and indicate, on the tomographic image, whether a speed of the change in the layer thickness increases or decreases by subtracting the difference between the layer thicknesses in the volume data pieces B and C from the difference between the layer thicknesses in the volume data pieces A and B. In this case, the color and the opacity may be set so that a portion with a large difference in the layer thickness becomes bluer and more opaque. Accordingly, a portion in which a rate of progression of disease becomes slower may be displayed bluer and more opaque. On the other hand, a portion in which the rate of progression of disease is less changed may be displayed using the voxel value of the volume data as it is. As a result, a doctor can easily confirm a portion where a treatment by a medication or an operation has exerted a rapid effect, and predict the progress of the change in the layer thickness.

In the present exemplary embodiment, the ophthalmologic image display apparatus 1 compares the volume data pieces captured by the tomographic image capturing apparatus 2. However, the ophthalmologic image display apparatus 1 may prepare a standard layer thickness of a retina by calculating, for example, an average value, an intermediate value, or a mode as statistics information from results of layer thickness measurements conducted on a plurality of healthy eyes. In this case, the ophthalmologic image display apparatus 1 measures a layer thickness in one piece of the volume data in step S501, and calculates a difference between the standard layer thickness and the measured layer thickness in step S502. As a result, the ophthalmologic image display apparatus 1 can indicate a portion deviating from a normal range of the layer thickness on the tomographic image, as illustrated in FIG. 6.

In this case, the line of the RPE and the line of the normal ILM may be displayed on the tomographic image. Further the color and opacity may be set so that a portion with a large difference in the layer thickness from the standard layer thickness prepared in advance becomes redder and more opaque. As a result, a portion with a layer thickness significantly deviating from the standard layer thickness can be displayed redder and more opaque. On the other hand, a portion with a similar layer thickness to the standard layer thickness can be displayed using the voxel value of the volume data as it is.

Accordingly, a doctor can compare the retina of a patient with a healthy eye on the tomographic image to recognize how much the condition of the retina of the patient has grown worse compared to the healthy eye. In addition, It is possible to calculate the difference between the thicknesses of the corresponding layers by normalizing a size of the tomographic image.

A second exemplary embodiment will be described based on an example of a method for performing volume rendering with use of volume data and layer thickness difference information. Volume rendering is a method for three-dimensionally visualizing, for example, an inner structure and a spatial distribution of temperature of an object displayed in the volume data by arbitrarily designing a transfer function for setting a color and an opacity. In the present exemplary embodiment, volume rendering is performed by designing a transfer function for setting a color and an opacity based on a layer thickness and a luminance value.

A processing procedure of the ophthalmologic image display apparatus 1 according to the present exemplary embodiment will be described with reference to the flowchart illustrated in FIG. 7. The processing similar to the processing illustrated in FIG. 5 will not be repeated here.

In step S703, the processing unit 12 designs transfer functions for a difference in the layer thickness and for a luminance value (corresponding to a value of a tomographic image). First, the transfer function for the difference in the layer thickness is designed in the following manner. More specifically, the transfer function for the difference in the layer thickness is designed so that the opacity of a portion in which the difference in the layer thickness is smaller than a predetermined value is set at a low level and to be gradually increased, and the opacity of a portion in which the difference in the layer thickness is larger than the predetermined value is set at a high level and to be rapidly increased. Further, the transfer function for the luminance value is designed so that the opacity is set at a low level and gradually increased and the color changes to blue, green, and red as the luminance value increases.

The design of the transfer functions and execution of volume rendering according thereto can result in such a display that the color becomes redder as the luminance value increases, and a portion with a large difference in the layer thickness becomes more opaque. Further, since the opacity is also set from the luminance value, it is possible to display three-dimensional distribution of a portion in which the difference in the layer thickness becomes larger in the entire retina.

In step S704, further, the processing unit 12 performs the volume rendering with use of the transfer functions designed in step S703.

According to the present exemplary embodiment configured as described above, it is possible to provide a display effective for a follow-up observation of an entire retina with use of a three-dimensional image by visualizing the three-dimensional distribution and the change amount of the layer thickness with respect to a portion where a disease has progressed and a portion where a treatment has exerted some effect.

In the above described respective exemplary embodiments, the present invention is embodied as the ophthalmologic image display apparatus. However, the exemplary embodiments of the present invention are not limited to the ophthalmologic image display apparatus. The present invention may be embodied in the form of, for example, a system constituted by a plurality of apparatuses, a device constituted by one apparatus, software and a program to be executed on a computer, or a storage medium such as an optical disk.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An apparatus comprising:
   at least one memory; and
   at least one processor configured to perform operations comprising:
   extracting corresponding retinal layers in at least two of tomographic images of a retina of an eye captured at different times;
   measuring retinal layer thicknesses of the extracted corresponding retinal layers;
   acquiring information indicating a difference between the measured retinal layer thicknesses;
   determining, as a partial region of the corresponding retinal layers, a region where the difference is larger than a threshold in at least one of the tomographic images;
   determining, based on the acquired information indicating the difference, a first color to a portion in which a retinal layer thickness is increased and a second color to a portion in which a retinal layer thickness is reduced; and
   causing a display unit to display at least one of the tomographic images, wherein the determined first and second colors are superimposed on the determined partial region of the at least one of the tomographic images.

2. The apparatus according to claim 1, wherein the at least two of tomographic images are two-dimensional tomographic images obtained by scanning the retina and using light reflected by the retina along an optical axis.

3. The apparatus according to claim 1, wherein the at least two of tomographic images are three-dimensional tomographic images obtained by scanning the retina including a plurality of two-dimensional images acquired by capturing two-dimensional images along an optical axis a plurality of times and using light reflected by the retina along a direction intersecting the optical axis.

4. The apparatus according to claim 1, wherein the determining unit determines a larger opacity as a change in the layer thickness with the passage of time increases.

5. The apparatus according to claim 1, wherein the determining unit uses an intensity value of the tomographic image as it is for a portion in which a change in the layer thickness with the passage of time is small, sets different colors to a portion in which a layer thickness is increased and a portion in which a layer thickness is reduced, and sets a larger opacity as the difference in the layer thickness increases.

6. The apparatus according to claim 1,
   wherein the determining unit determines colors at different positions in the at least one of the tomographic images based on the acquired information indicating the difference, and
   wherein the display control unit causes the display unit to display the at least one of the tomographic images using the determined colors.

7. The apparatus according to claim 1, wherein the corresponding retinal layers are nerve fiber layers of the eye.

8. A method comprising:
   extracting corresponding layers in at least two of tomographic images of a retina of an eye captured at different times;
   measuring retinal layer thicknesses of the extracted corresponding retinal layers;
   acquiring information indicating a difference between the measured retinal layer thicknesses;
   determining, as a partial region of the corresponding retinal layers, a region where the difference is larger than a threshold in at least one of the tomographic images;
   determining, based on the acquired information indicating the difference, a first color to a portion in which a retinal layer thickness is increased and a second color to a portion in which a retinal layer thickness is reduced; and
   causing a display unit to display at least one of the tomographic images, wherein the determined first and second colors are superimposed on the determined partial region of the at least one of the tomographic images.

9. A non-transitory computer-readable storage medium for storing a computer program for causing a computer to execute a method according to claim 8.

10. The method according to claim 8, wherein the at least two of tomographic images are two-dimensional tomographic images obtained by scanning the retina and using light reflected by the retina along an optical axis.

11. The method according to claim 8, wherein the at least two of tomographic images are three-dimensional tomographic images obtained by scanning the retina including a plurality of two-dimensional images acquired by capturing two-dimensional images along an optical axis a plurality of times and using light reflected by the retina along a direction intersecting the optical axis.

12. The method according to claim 8, wherein a larger opacity is determined as a change in the layer thickness with the passage of time increases.

13. The method according to claim 8, wherein in determining opacities an intensity value of the tomographic image is used as it is for a portion in which a change in the layer thickness with the passage of time is small, different colors are set to a portion in which a layer thickness is increased and a portion in which a layer thickness is reduced, and a larger opacity is set as the difference in the layer thickness increases.

14. The method according to claim 8,
   wherein colors at different positions in the at least one of the tomographic images are determined based on the acquired information indicating the difference, and
   wherein the display unit is caused to display the at least one of the tomographic images using the determined colors.

15. The method according to claim 8, wherein the corresponding layers are nerve fiber retinal layers of the eye.

* * * * *